United States Patent
Fay et al.

(10) Patent No.: US 8,054,092 B2
(45) Date of Patent: Nov. 8, 2011

(54) CORROSION DETECTING STRUCTURAL HEALTH SENSOR

(75) Inventors: Matthew K. Fay, Wentzville, MO (US); Greg L. Sheffield, O'Fallon, MO (US)

(73) Assignee: The Boeing Company, Chicago, IL (US)

( * ) Notice: Subject to any disclaimer, the term of this patent is extended or adjusted under 35 U.S.C. 154(b) by 454 days.

(21) Appl. No.: 11/941,367

(22) Filed: Nov. 16, 2007

(65) Prior Publication Data
US 2009/0128169 A1    May 21, 2009

(51) Int. Cl.
*G01R 27/08* (2006.01)
(52) U.S. Cl. ......................................................... 324/700
(58) Field of Classification Search .................... 324/700
See application file for complete search history.

(56) References Cited

U.S. PATENT DOCUMENTS

| | | | |
|---|---|---|---|
| 3,599,090 A * | 8/1971 | Fitzpatrick et al. | 324/508 |
| 4,087,800 A | 5/1978 | Lee | |
| 4,587,517 A | 5/1986 | Engstrom et al. | |
| 5,144,973 A * | 9/1992 | Green et al. | 137/71 |
| 5,936,525 A * | 8/1999 | Leyden et al. | 340/568.2 |
| 5,977,782 A * | 11/1999 | Kordecki | 324/700 |
| 6,501,286 B1 * | 12/2002 | Balfanz et al. | 324/700 |
| 7,068,052 B2 * | 6/2006 | Hilleary et al. | 324/700 |
| 7,132,943 B2 | 11/2006 | Nelson | |
| 7,231,826 B2 | 6/2007 | Bossi et al. | |
| 7,333,898 B2 | 2/2008 | Griess et al. | |
| 7,388,166 B2 | 6/2008 | Marmaropoulos et al. | |
| 7,434,480 B2 | 10/2008 | Georgeson et al. | |
| 7,621,193 B2 * | 11/2009 | Fay et al. | 73/865.9 |
| 2002/0145529 A1 | 10/2002 | Kuzik et al. | |
| 2004/0130340 A1 * | 7/2004 | Tiefnig | 324/700 |
| 2006/0144997 A1 | 7/2006 | Schmidt et al. | |
| 2007/0125189 A1 | 6/2007 | Bossi et al. | |
| 2007/0144272 A1 | 6/2007 | Yu et al. | |
| 2007/0252718 A1 | 11/2007 | Ray | |
| 2008/0109187 A1 | 5/2008 | Kollgaard et al. | |
| 2008/0163670 A1 | 7/2008 | Georgeson | |
| 2008/0167833 A1 | 7/2008 | Matsen et al. | |
| 2008/0223152 A1 | 9/2008 | Georgeson et al. | |

FOREIGN PATENT DOCUMENTS

| | | |
|---|---|---|
| JP | 1054244 | 8/1987 |
| JP | 2005055331 | 8/2003 |
| JP | 2007292747 | 3/2006 |
| WO | WO94/09354 | 4/1994 |

OTHER PUBLICATIONS

UK Patent Application No. GB0820180.8 Combined Search and Examination Report, Mar. 2, 2009, pp. 1-5.

(Continued)

*Primary Examiner* — Jeff Natalini
(74) *Attorney, Agent, or Firm* — Canady & Lortz LLP; Bradley K. Lortz

(57) ABSTRACT

A sensor device for monitoring and testing for potential corrosion of structural elements is disclosed. A membrane including a thin conductor sense loop within it may be disposed near a structural element to be monitored. Measured changes in the electrical properties of the conductor sense loop reveal corrosion of the conductor and can indicate potential corrosion in the structural element. The sensor may also be implemented as a gasket. Connection to the sensor device may be through a connector or using a wireless reader which remotely energizes the sensor device.

17 Claims, 8 Drawing Sheets

OTHER PUBLICATIONS

Greene, "Sensors Without Batteries," http://www.technologyreview.com/read_article.aspx?id=16864&ch=infotech&a=f, Technology Review Published by MIT, May 15, 2006.

Eckfeldt, "What Does RFID Do for the Consumer?," Comm. of the ACM, Sep. 2005, vol. 48, No. 9, pp. 77-79.

Gunther et al., "RFID and the Perception of Control: The Consumer's View," Comm. of the ACM, Sep. 2005, vol. 48, No. 9, pp. 73-76.

Ohkubo et al., "RFID Privacy Issues and Technical Challenges," Comm. of the ACM, Sep. 2005, vol. 48, No. 9, pp. 66-71.

Hsi et al., "RFID Enhances Visitors' Museum Experience at the Exploratorium," Sep. 2005, vol. 48, No. 9, pp. 60-65.

Pering et al., "Spontaneous Marriages of Mobile Devices and Interactive Spaces," Sep. 2005, vol. 48, No. 9, pp. 53-59.

Sample et al., "Design of an RFID-Based Battery-Free Programmable Sensing Platform," IEEE Trans. on Instr. and Meas., vol. 57, No. 11, Nov. 2008, pp. 2608-2615.

Raskar et al., "Photosensing Wireless Tags for Geometric Procedures," Sep. 2005, vol. 48, No. 9, pp. 46-51.

Smith et al., "RFID-Based Techniques for Human-Activity Detection," Sep. 2005, vol. 48, No. 9, pp. 39-44.

Borriello, "RFID: Tagging the World," Sep. 2005, vol. 48, No. 9, pp. 34-37.

* cited by examiner

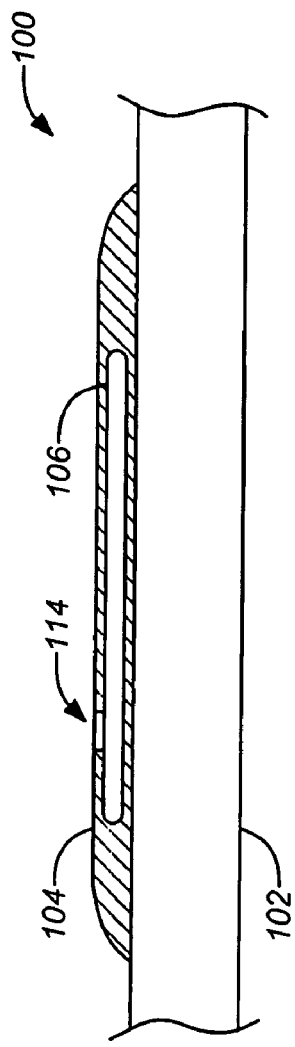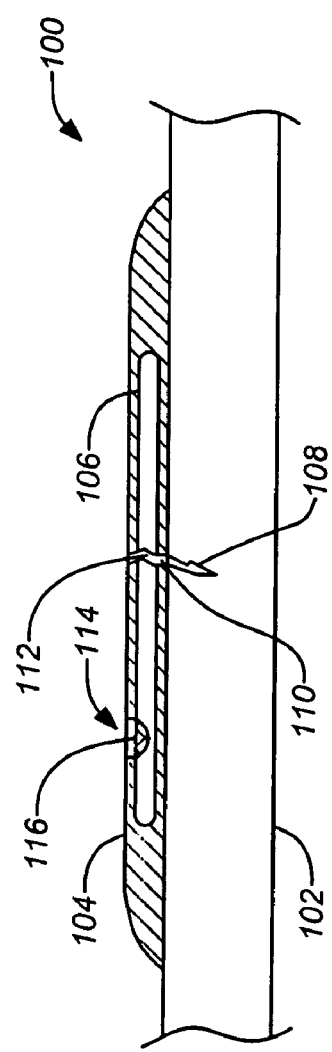

CORROSION DETECTING STRUCTURAL HEALTH SENSOR

CROSS-REFERENCE TO RELATED APPLICATIONS

This application is related to U.S. patent application Ser. No. 11/941,307, by Fay et al. filed on this same day, and entitled "FRACTURE DETECTING STRUCTURAL HEALTH SENSOR".

BACKGROUND OF THE INVENTION

1. Field of the Invention

This disclosure relates to structural testing. Particularly, this disclosure relates to techniques for monitoring corrosion of structural elements over time in service.

2. Description of the Related Art

The need to monitor the integrity of structural elements arises in many different applications. For example, it is necessary to monitor the structures of aircraft. The aircraft stay in service for many years and may experience environments that may exceed design limits resulting in different types of failures, e.g., fatigue, fracture, corrosion. Therefore, it is necessary to regularly check the structural integrity of the vehicle as part of any prudent maintenance program. Similarly, other types of structures may also require regular monitoring. Highway structures such as overpasses and bridges must be regularly checked. Some building structures may also require regular testing. Conventional testing techniques such as visual inspection, x-ray, dye penetrant, and electrical field techniques (e.g. eddy current testing, etc.) for testing structural elements have many drawbacks.

Visual inspection of structural members often requires some degree of disassembly of the structure. This adds greatly to the overall testing cost. For example, visual inspection for aircraft structures requires substantial disassembly of structure and removal of installed equipment in order to provide the access needed to view the areas of interest at a distance adequate to detect corrosion visually.

X-Ray testing, under the broader heading of radiographic testing, requires specialized facilities and government licenses. The technique employs the ability of short wavelength electromagnetic radiation to penetrate various materials. Either an X-ray machine or a radioactive source can be used as a source of photons. Because the amount of radiation emerging from the opposite side of an examined material can be detected and measured, variations in the intensity of radiation are used to determine thickness or composition of material and reveal any defects. Due to safety issues, X-ray testing also typically requires a complete work stoppage on all other tasks while the testing is being performed.

Dye penetrant testing is also time consuming and messy. Dye penetrant inspection is used to reveal surface breaking flaws through the bleedout of a colored or fluorescent dye from the flaw. The technique is based on the ability of a liquid to be drawn into a surface breaking flaw by capillary action. After a period of time, excess surface penetrant is removed and a developer is applied. This acts as a blotter. It draws the penetrant from the flaw to reveal its presence. The constituent penetrant and developer may and their by-products may be identified as hazardous (HAZMAT), requiring costly disposal means.

Finally, inspection methods using the application of electrical fields (e.g., eddy current testing, etc.) are exceptionally time consuming and difficult to read reliably in this type of application and may require alterations to structure. In typical eddy current testing for example, a circular coil carrying an AC current is placed in close proximity to an electrically conductive specimen to be tested. The alternating current in the coil yields a changing magnetic field, which interacts with the test object and induces eddy currents in it. Variations in the phase and magnitude of these eddy currents can be monitored using a second coil, or by measuring changes to the current flowing in the primary coil. The presence of any flaws or variations in the electrical conductivity or magnetic permeability of the test object, will cause a change in eddy current flow and a corresponding change in the phase and amplitude of the measured current. The technique is generally limited to detecting surface breaks or near surface cracking and variations in material composition.

In view of the foregoing, there is a need in the art for apparatuses and methods for efficiently monitoring the integrity of structural elements. In particular, there is a need for such apparatuses and methods to monitor corrosion of structural elements without requiring time-consuming disassembly. There is also a need for such apparatuses to be light weight. And there is further a need for such apparatuses and methods to be inexpensive to implement and use. There is particularly a need for such systems and apparatuses in aircraft applications. These and other needs are met by the present disclosure as detailed hereafter.

SUMMARY OF THE INVENTION

A sensor device for monitoring and testing for potential corrosion of structural elements is disclosed. A membrane including a thin conductor sense loop within it may be disposed near a structural element to be monitored. Measured changes in the electrical properties of the conductor sense loop reveal corrosion of the conductor and can indicate potential corrosion in the structural element. The sensor may also be implemented as a gasket. Connection to the sensor device may be through a connector or using a wireless reader which remotely energizes the sensor device.

A typical embodiment of the invention comprises an apparatus for sensing corrosion, including a non-conductive material layer, a conductor sense loop within the non-conductive material layer and having a portion exposed through a weep hole in the non-conductive material layer, the conductor sense loop having ends, and a connecting device coupled to the ends of the conductor sense loop. The exposed portion of the conductor sense loop corrodes to induce a change in an electrical property of the conductor sense loop sensed through the connecting device. The conductor sense loop corroding may be used to indicate potential corrosion of a near structural surface. In some embodiments of the invention, the non-conductive material layer may be disposed between a structural surface and a second structural surface, e.g. as in a gasket configuration. In this case, the non-conductive material layer may also included one or more sealing ribs against at least one of the structural surface and the second structural surface.

In some embodiments of the invention, the non-conductive material layer may comprise two layers sandwiching the conductor sense loop. In addition, the conductor sense loop may be routed around a fastener hole. The non-conductive material layer may be constructed from a resilient material, e.g. a soft material such as silicon. Alternately, the non-conductive material layer may be a frangible material. Typically, the non-conductive material layer may be bonded to a structural surface as it is installed. In some embodiments of the invention, the connecting device may comprise a wireless communications tag.

In a similar manner, a typical method embodiment of the invention for sensing corrosion, includes the steps of exposing a portion a conductor sense loop through a weep hole in a non-conductive material layer, the conductor sense loop being disposed within the non-conductive material layer, coupling a connecting device to ends of the conductor sense loop, and sensing a change in an electrical property of the conductor sense loop through the connecting device to indicate corrosion of the exposed portion of the conductor sense loop. Method embodiments of the invention may be further modified consistent with the apparatus embodiments described herein.

The features, functions, and advantages that have been discussed can be achieved independently in various embodiments of the present invention or may be combined in yet other embodiments further details of which can be seen with reference to the following description and drawings.

BRIEF DESCRIPTION OF THE DRAWINGS

Referring now to the drawings in which like reference numbers represent corresponding parts throughout:

FIG. 1A illustrates a side view of an exemplary membrane corrosion sensor installed on a structural element;

FIG. 1B illustrates a side view of the exemplary membrane corrosion sensor indicating a corrosion;

DETAILED DESCRIPTION OF THE PREFERRED EMBODIMENT

1. Overview

Figure 1C:
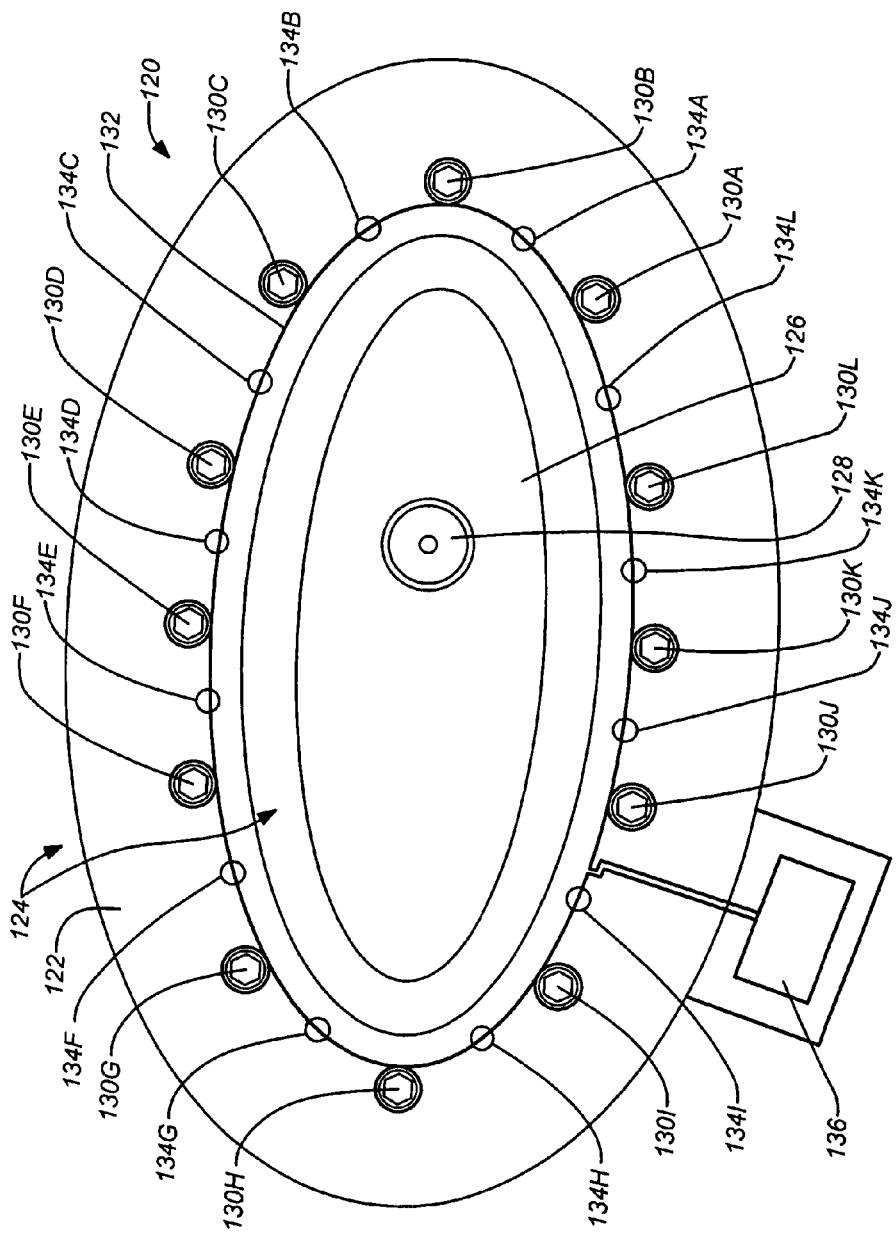
FIG. 1C illustrates a top view of an exemplary membrane corrosion sensor.

As previously mentioned, embodiments of the invention are directed to a technique for detecting a discontinuity or change in sense loop electrical properties caused by corrosion of the conductor sense loop. This may be used to indicate the potential for corrosion of surrounding structural elements, e.g. metal structural components of an aircraft. The sensor comprises a membrane with an embedded conductor sense loop that is at least partially exposed through one or more weep holes. The membrane may be bonded to a structural element and/or sandwiched between two structural elements in a gasket configuration. This corrosion sensor may also be combined with a structural damage sensor using a frangible membrane material and a breakable conductor sense loop as also described herein. Connection to the conductor sense loop can be made through an ordinary electrical connector or a wireless communication tag.

Thus, a membrane corrosion sensor can detect hidden fractures and other structural damage without any component or structural disassembly. In the absence of damage severe enough to require repair, embodiments of the invention eliminate any required disassembly of components or structures as would otherwise be required to perform routine visual inspections. Further, embodiments of the invention do not require special facilities, training or government licenses. Embodiments of the invention also provide a quicker process for determining whether structural defects are present without interrupting other work in progress.

A gasket corrosion sensor in accordance with an embodiment of the invention can lower the total cost of ownership for an aircraft or other vehicle based on the labor it can save and the additional equipment availability it can provide. Operators will not have to take equipment out of service, provided that there are no incidents of damage that need to be repaired. In contrast, conventional methods require copious labor and extended periods out of service to accomplish—even if no repairs are required. Conventional methods also enhance the risk of maintenance induced damage during the disassembly required for access.

2. Membrane Corrosion Sensor

FIG. 1A illustrates a side view of an exemplary corrosion membrane sensor 100 installed on a structural element 102. The corrosion sensor 100 comprises a membrane material 104 formed into a thin flat structure that may be disposed adjacent to the surface of a structural element 102. Typically the membrane material is bonded to the structural element. A conductor sense loop 106 is embedded within the membrane material 104. The membrane material 104 includes one or more weep holes 114 which penetrate to expose the conductor sense loop 106. For corrosion sensing, the membrane material need only support the conductor sense loop 106; it may be rigid or soft, although a resilient material is preferred to make the sensor 100 more durable. The exposed portion of the conductor sense loop 106 is used to sense corrosion as described with respect to FIG. 1B.

FIG. 1B illustrates a side view of the exemplary membrane corrosion sensor 100 indicating corrosion using one or more weep holes 114. Corrosion that develops on the portion of the conductor sense loop 106 exposed by the weep holes 114 in the membrane material 104 effects electrical properties of the conductor sense loop 106. The change in the electrical properties of the conductor sense loop 106 (e.g., resistance, inductance, capacitance or an open circuit indicating corrosion) can then be measured to sense the corrosion. The particular measured electrical property may be varied depending upon the application. In one example implementation, the membrane may be constructed from two layers of thin plastic film which contains the one or more fine wire sense loops sandwiched between. The membrane is a non-conductive material that is self adhesive at installation and effectively seals and protects the underlying structure from corrosion.

For example, the conductor material may be selected to be particularly susceptible to corrosion so that any moisture that comes in contact with the area will enter the weep hole 114 and cause at least a partial reduction of the exposed portion of the breakable conductor sense loop 106. This will result in an increase in the effective resistance of the conductor as the cross sectional area of the conductor is reduced by the corrosion. Thus, although actual corrosion of the structural element 102 may not yet exist, the weep hole 114 allows the conductor sense loop 106 to provide an early warning of possible corrosion to the structural element due to the presence of moisture. It should be noted that design of the conductor sense loop 106 may be optimized such that the portions of the conductor sense loop 106 may be treated differently or comprise a different material than the unexposed portions of the conductor sense loop 106 to enhance the corrosion sensitivity in this area. The ends of the conductor sense loop 106 are connected to a connecting device which is coupled to a sensing circuit that detects the corrosion (or optionally, fractures as well) as illustrated in the following FIG. 1C.

The membrane material should be non-porous. The membrane material should be both an effective electrical insulator and flexible enough to permit ease of installation. The membrane material should have good shelf-life qualities to permit stocking of spares. The membrane material must be non-corrosive. The membrane material and conductor sense loop material and size and selected electrical measurement parameters may be tailored to a specific installation application in order to maximize gasket and sensing performance as will be understood by those skilled in the art. Materials for the frangible membrane may have characteristics similar to paint coatings in appearance and include, but are not limited to polycarbonate, urethane, polyurethane, enamel, polyester, acrylic, epoxy, and a wide variety of plastics and other similar materials.

In addition to corrosion sensing, the sensor 100 may also be further adapted to detect other structural defects occurring in the adjacent structural element 102. To do this however, the conductor sense loop 106 of the corrosion sensor 100 must also be breakable conductor sense loop 106 and the membrane material 104 must be frangible. The frangible membrane material 104 must be non-conductive so as not to short the breakable conductor sense loop 106 which is employed to detect a fracture or other structural failure in the surface of the structural element 102. In this case, a fracture 108 appearing in the surface of the structural element 102 induces a break 110 in the frangible material 104 which in turn carries through to cause a break 112 in the breakable conductor sense loop 106.

FIG. 1C illustrates a top view of an exemplary membrane corrosion sensor 120. In this example, the membrane 122 is applied to the surface of a structural element 124 that is the metal skin of an aircraft at a location that has an antenna base 126 mounted. The airfoil 126 carries the antenna connector 128 within it and is bolted to the aircraft skin (structural element 124) by a series of bolts 130A-130L around the perimeter of the antenna base 126. The conductor sense loop 132 is embedded within the membrane 122 as previously described. Multiple weep holes 134A-134L at various locations along the conductor sense loop 132 permit one or more exposed portions of the conductor sense loop 132 to corrode as previously described to provide an early warning of potential corrosion to nearby structural elements.

The conductor sense loop 132 of the sensor 120 is coupled to a connecting device 136 which is used to connect to a reader device that measures changes in the electrical properties of the conductor sense loop 132. In the simplest implementation, the connecting device 135 may comprise a simple electrical connector. However, the connecting device 135 may also comprise a wireless communication tag as described hereafter which affords many advantages beyond a simple electrical connector. The reader device can be any known device capable of measuring the electrical properties of the conductor sense loop 132. The wireless communication tag incorporates some of the reader device with the tag.

The membrane 122 may be installed at structural locations where corrosion is a concern. At appropriate intervals, an operator uses a reader device to energize and read the membrane sensor 120. Either a wireless reader device or another external device may be used to compare the readings of a conductor sense loop to those of a reference value measured at each specific installation to determine if corrosion or damage is present. The reference value can be determined when the membrane or gasket sensor is designed for a specific application and manufactured. The reference value for the specifice application can either exist in written form for manual measurement and analysis or be loaded into the wireless reader for automatic analysis.

In another example implementation, the sensor comprises a membrane material that is frangible after installation to also provide sensing of fractures or other structural failures in the underlying structural element. In this case, the objective is that the composition of the frangible membrane should match the structure material it is bonded to such that if a crack occurs in the structural element, the frangible membrane cracks as well, breaking (or otherwise disrupting) the conductor which forms the sense loop. For fracture detection, the conductor sense loop 132 is generally position transversely across locations where a fracture is most likely. For example, in FIG. 1C the conductor sense loop 132 takes a route around the perimeter of the antenna airfoil 126 where any structural failures are likely to appear. In a like manner, the conductor sense loop 132 is routed around each of the bolts 130A-130L in small loops.

The frangible membrane may be either a pre-formed device or fabricated on site. The frangible membrane material should be an effective electrical insulator and flexible enough prior to installation to permit ease of installation. The frangible membrane material should have good shelf-life quality to permit stocking of spares. The frangible membrane material must be non-corrosive, particularly to the breakable conductor sense loop. The frangible membrane and sense loop materials and sizes and electrical measurement characteristics can be selected for a specific installation to maximize membrane performance. Materials for the frangible membrane may have characteristics similar to paint coatings in appearance and include, but are not limited to polycarbonate, urethane, polyurethane, enamel, polyester, acrylic, epoxy, and a wide variety of plastics and other similar materials.

The sense loop may be custom tailored to the specific application. It can typically be constructed from the same material (e.g., base metal and alloy) as the structural element at the installed interface. The configuration and size of the sense loop should be appropriate to ensure the conductor breaks when and if the membrane fractures. Materials for the sense loop include, but are not limited to aluminum, steel, copper, magnesium, titanium, and other similar materials. A membrane sensor device may also be implemented in a gasket configuration as described in the next section.

3. Gasket Corrosion Sensor

Figure 2A:
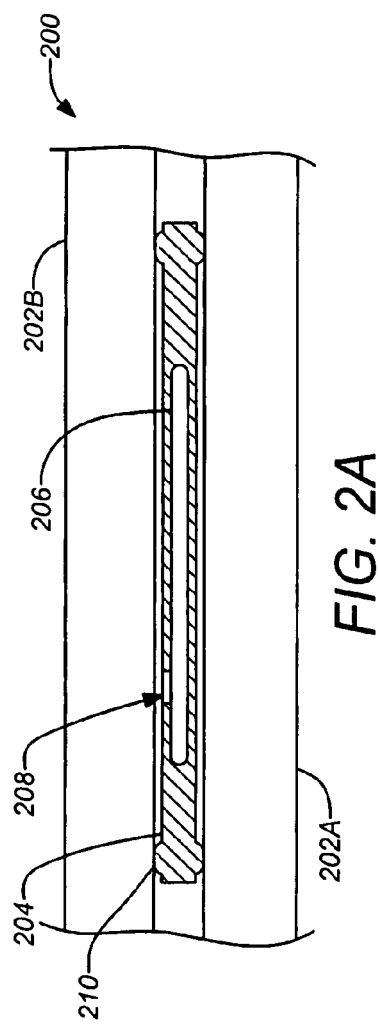
FIG. 2A illustrates a side view of an exemplary corrosion sensor in a gasket configuration.

FIG. 2A illustrates a side view of an exemplary membrane corrosion sensor 200 in a gasket. The sensor 200 comprises a membrane material 204 formed into a thin flat structure that is disposed adjacent to the surfaces of two structural elements 202A, 202B. In this case, the membrane material is sandwiched between the structural elements 202A, 202B. A conductor sense loop 206 is embedded within the membrane material 204. Here also, the membrane material 204 must be non-conductive so as not to short the conductor sense loop 206 employed to detect potential corrosion of either of the structural elements 202A, 202B. The membrane material 204 includes one or more weep holes 208 which penetrate to expose the conductor sense loop 206. The conductor sense loop 206 is used to provide early detection of corrosion as previously described. The gasket configuration of the sensor 200 can also include one or more ribs 210 built into one or both sides of the frangible material 204. The ribs 210 are designed to provide a seal against one or both surfaces of the structural elements 202A, 202B.

Figure 2B:
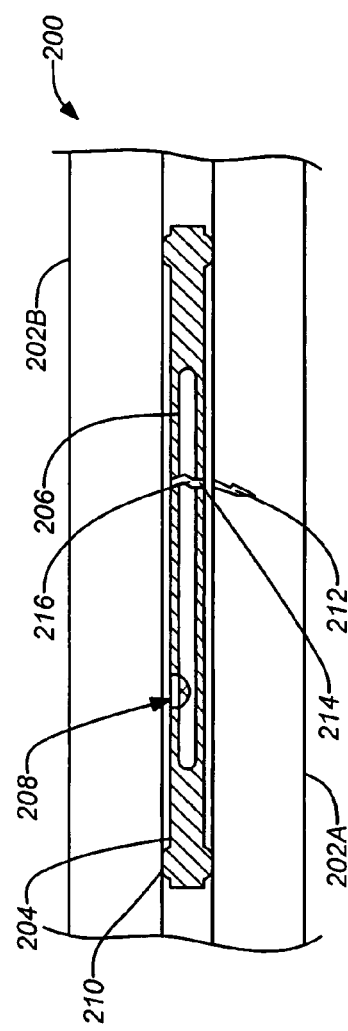
FIG. 2B illustrates a side view of an exemplary corrosion sensor in a gasket indicating corrosion.

FIG. 2B illustrates a side view of the exemplary membrane corrosion sensor 200 in a gasket indicating corrosion. As previously described, the conductor material may be selected to be susceptible to corrosion so that any moisture that comes in contact with the area will enter the weep hole 208 and cause at least a partial erosion of the conductor. For example, this may be used to cause an increase in the effective resistance of the conductor as the cross sectional area of the conductor is reduced by the corrosion. Thus, although actual corrosion of the structural elements 202A, 202B may not exist yet, the weep hole 208 allows the conductor sense loop 206 to provide an early warning of possible corrosion to either structural element 202A, 202B due to the presence of moisture.

It should be noted that the gasket configuration is particularly well suited for early corrosion detection because the both surfaces of the membrane material 204 are intended to remain sealed from the environment (with or without the sealing ribs 210). Thus, any moisture present in the weep holes 208 would not be evident even under a visual inspection. Finally, the ends of the conductor sense loop 106 are connected to a connecting device which is coupled to a sensing circuit that detects the corrosion.

If fracture sensing is also desired, the membrane material 204 must also be frangible and the conductor sense loop 206 breakable as previously described. A fracture 212 appearing in the surface of at least one structural element 202A induces a break 214 in the frangible material 204 which in turn carries through to cause a break 216 in the breakable conductor sense loop 206. Corrosion that develops in the weep holes 208 in the frangible material 204 may cause a break in the breakable conductor sense loop 206 as well.

Figure 2C:
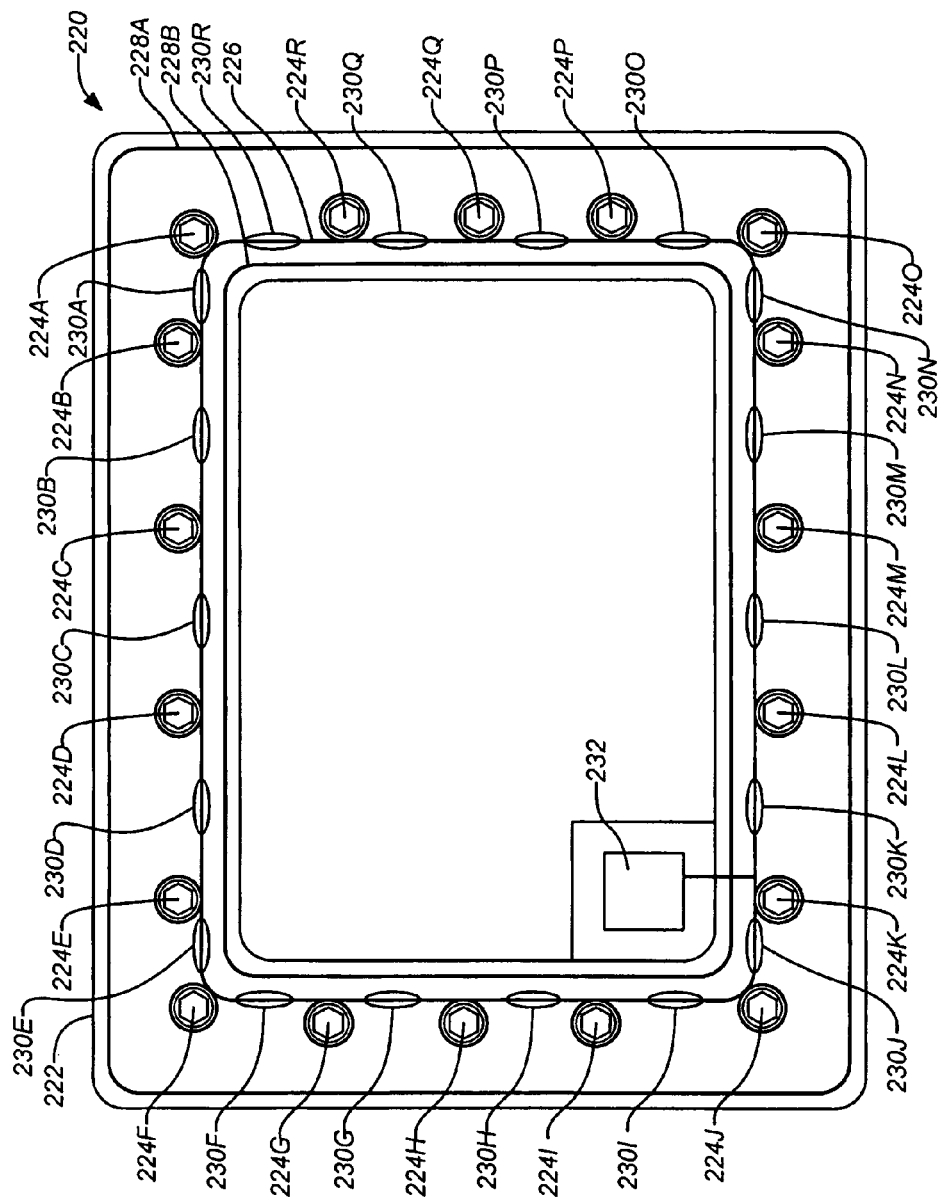
FIG. 2C illustrates a top view of an exemplary corrosion sensor in a gasket configuration.

FIG. 2C illustrates a top view of an exemplary membrane corrosion sensor 220 in a gasket. Communication with the sensor 220 may be accomplished using any known technique. In this configuration, a membrane 222 is sandwiched between the surfaces of two structural elements as described in FIGS. 2A and 2C. For example, the structural elements may be a joint between two components of an aircraft. A series of bolts 224A-224R are disposed around the interface between the structural elements. The conductor sense loop 226 is embedded within the membrane 222 as previously described and is routed around the interface as well. Weep holes 230A-230R at various locations along the breakable conductor sense loop 226 which operate as previously described to provide an early warning of potential corrosion. Ribs 228A, 228B are also laid out around the perimeter of both the inner and outer edges of the gasket membrane 222 (on one or both sides of the membrane as previously described in FIGS. 2A and 2B) to seal the membrane surface and the structural element surfaces from moisture.

The conductor sense loop 226 of the gasket sensor 220 is coupled to a connecting device 232 which is used to connect to a reader device that measures changes in the electrical properties of the conductor sense loop 226 indicating corrosion. The reader device can be any known device capable of measuring the electrical properties of the conductor sense loop 226. In a simple implementation, the connecting device 232 may comprise an electrical connector. However, the connecting device 232 may also comprise a wireless communication tag as described in the next section which affords many advantages beyond a simple electrical connector. The wireless communication tag incorporates some of the reader device with the tag.

The gasket may be installed at structural interfaces where corrosion inspections were previously scheduled, or areas of interest. The gasket remains installed serving to seal the interface against the intrusion of liquids and other contaminants. The gasket is entirely benign in its installed environment with respect to corrosion and emitted energy. At appropriate intervals, the operator uses a wireless reader device to energize and read the gasket. Either a wireless reader or another external device will compare the readings of the one or more conductor sense loops to those of the reference value measured at each specific installation to determine if corrosion or damage is present. The reference value can be determined when the membrane or gasket sensor is designed for a specific application and manufactured. The reference value for the specific application can either exist in written form for manual measurement and analysis or be loaded into the wireless reader for automatic analysis.

The gasket may be designed to form an effective seal for the faying surface of the joint in order to mechanically prevent liquids from intruding. The gasket material should be non-porous and resilient (i.e., returns to original shape after becoming deformed by applied pressure) over several inspection intervals. The gasket material should be both an effective electrical insulator and flexible enough to permit ease of installation. The gasket material should have good shelf-life qualities to permit stocking of spares. The gasket material must be non-corrosive. The gasket material and conductor sense loop material and size and selected electrical measurement parameters may be tailored to a specific installation application in order to maximize gasket and sensing performance. Materials for the gasket include, but are not limited to silicone, rubber, nitrile, Buna-N, neoprene, Teflon, and other similar materials.

The sensor 220 may also be used for fracture detection using a frangible membrane and breakable conductor sense loop 226 in combination with corrosion sensing. In this case, the breakable conductor sense loop 226 should be laid perpendicular to where any structural failures are likely to appear. Thus, the breakable conductor sense loop 226 is routed around each of the bolts 224A-224R in small loops.

4. Wireless Communication with Sensor

Figure 3A:
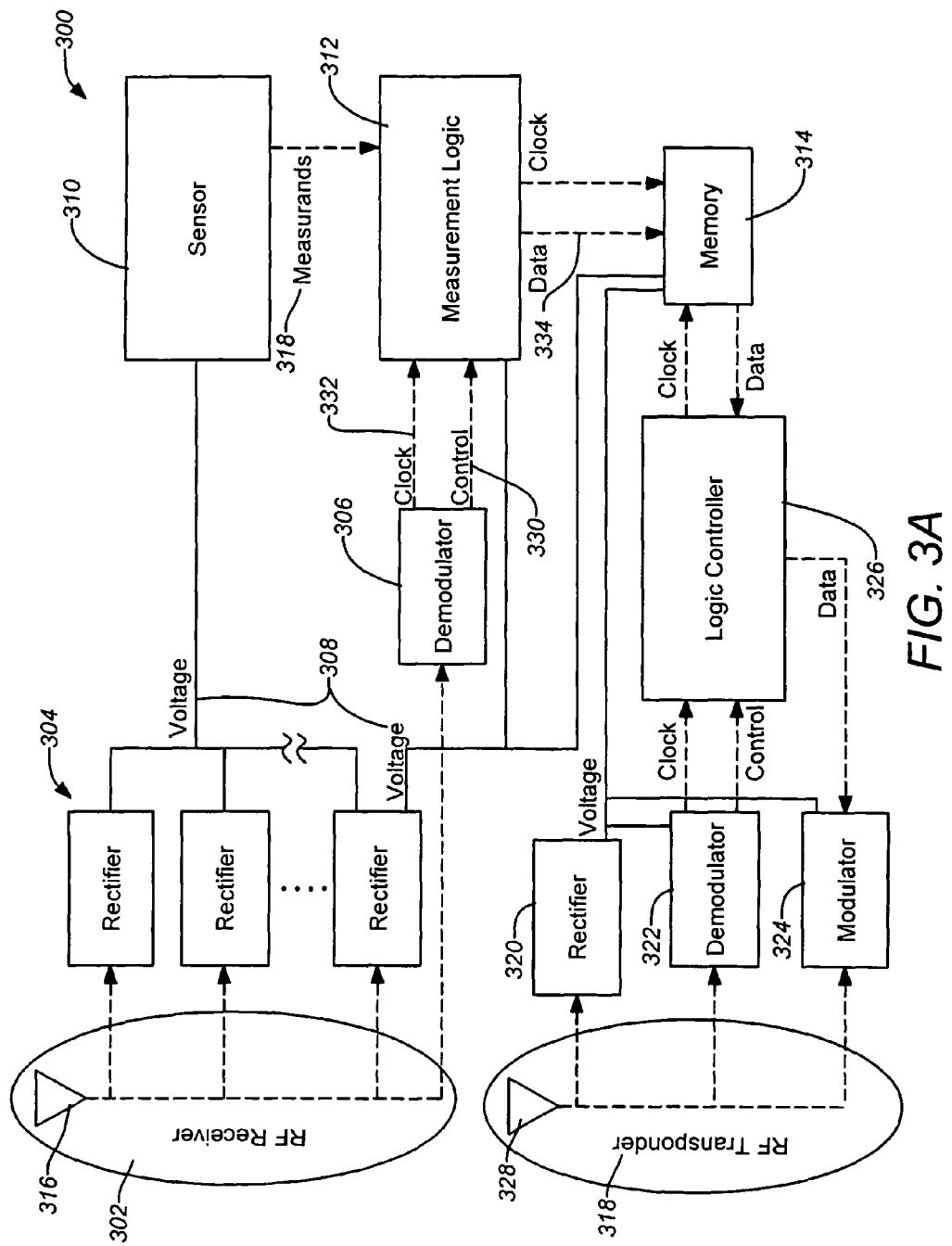
FIG. 3A illustrates a wireless communication tag that may be coupled to a corrosion sensor.

FIG. 3A illustrates a wireless communication tag 300 that may be coupled to a structural sensor 310. The example wireless communications tag 300 comprises one or more RF receivers 302. The one or more receivers 302 are coupled to a series of rectifier circuits 304 and a demodulator 306. The RF receivers should be designed with one or more resonant frequencies to maximize the excitation of the receiver rectifier circuits and demodulators. Each RF receiver rectifier circuit 304 may be associated with a specific series and/or parallel resonant frequency to maximize signal voltage 308 generated to power necessary sections of the tag and sensor 310 (i.e., the sense loop) during different modes of operation. Voltage 308 from the rectifiers 304 is supplied to the sensor 310 that yields measurands 318 to the measurement logic circuit 312. The clock 302 and control 330 signals from the demodulator 306 are used to control the measurement logic 312 to convert measurands 318 into data 334 transferred to memory 314. The demodulator 306 clock 332 is used to generate the clock signal from the measurement logic 312 for clocking data into memory 314. The clock and control signals from the demodulator 322 are used to control the logic controller 326 to read and write data into memory 314.

The RF receiver 302 may comprise one or more series and/or parallel resonant frequencies for the receiver demodulator 306 to properly control and synchronize the measurement logic 312 and targeted locations of the memory 314. The RF receiver 302 antenna 316 may support a series and parallel resonant frequencies by using a distributed capacitance, inductance, and resistance as known in the art. The RF receiver 302 may be designed to operate using OFDM, CDMA or any other multi-carrier resonant frequencies across the frequency spectrum known in the art. The RF receiver 302 should be designed with safeguard features to ensure inappropriate operations do not occur based on safety requirements.

Figure 3B:
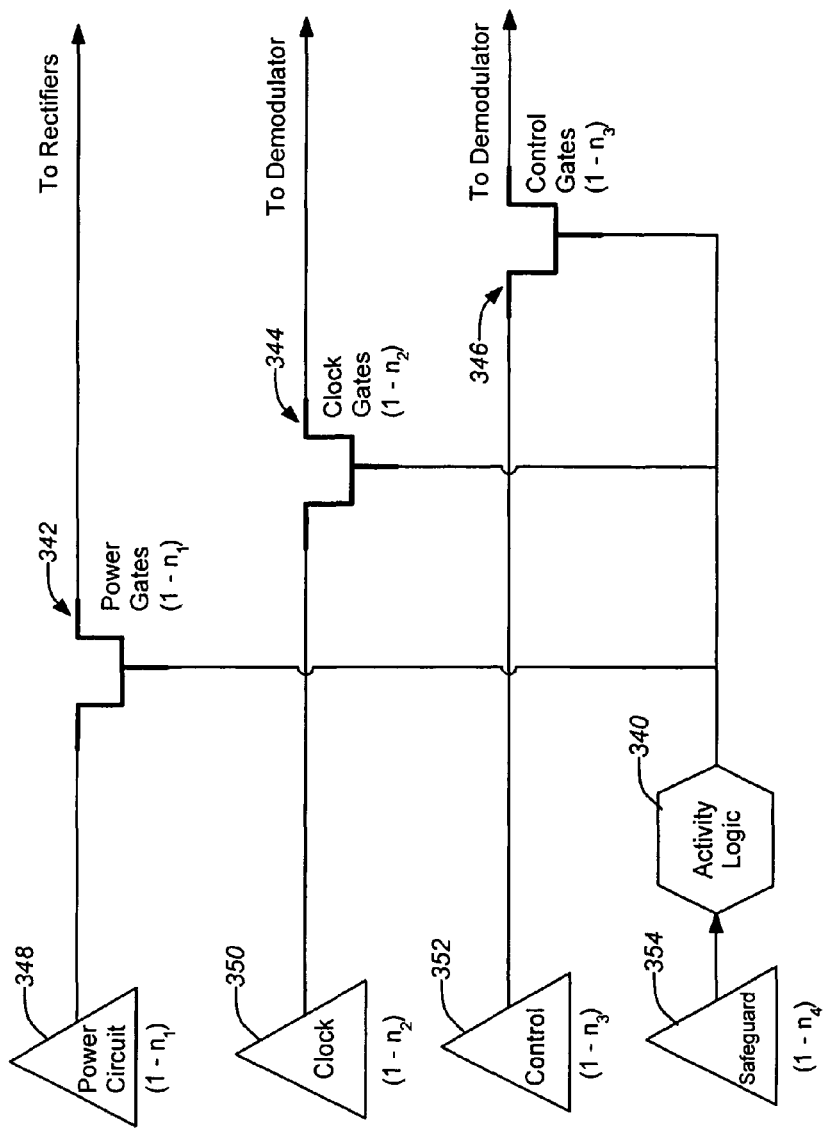
FIG. 3B illustrates an example safeguard feature for an receiver in a wireless communication tag.

FIG. 3B illustrates an example safeguard feature for a receiver 302 (such as the RF receiver 302 of FIG. 3A) in a wireless communication tag 300. Sets of unique resonant frequency (or frequency pattern) inputs 348 ($1$-$n_1$), 350 ($1$-$n_2$), 352 ($1$-$n_3$) are used to respectively direct the power, clock and control of the device. Typically, the sets of power resonant frequency inputs 348 direct the rectifiers (e.g., rectifiers 304 of FIG. 3A), while the the sets of clock and control resonant frequency inputs 350, 352 direct the demodulator (e.g., demodulator 306 of FIG. 3A) of the device. Embodiments of the invention may further implement a safeguard feature for preventing inadvertent activities of the overall device may use a set of safeguard resonant frequency inputs 354 ($1$-$n_4$) per device. (The safeguard resonant frequency inputs 354 may be either unique resonant frequency patterns or a subset of the frequencies used from the power, clock, and/or control resonant frequencies inputs 348, 350, 352.) The activity logic 340 operates to enable the power, clock and control gates 342, 344, 346, respectively, only when the set of safeguard resonant frequency inputs 354 (e.g., specific frequencies with corresponding amplitudes) meet the required safeguard conditions of the activity logic circuit 340. For example, the activity logic 340 may require specific timing or sequencing of the receiving sets of frequency inputs 348, 350, 352, 354. The safeguard conditions may be statically part of the activity logic circuit 340 or implemented in a way that allows for reconfiguration, e.g., through a programmable element.

Those skilled in the art will appreciate that a similar safeguard architecture can be readily applied for an transponder (such as the RF transponder 318 of FIG. 3A). The RF transponder 318 should be designed with one or more resonant frequencies to maximize the excitation of the one or more transponder rectifier circuits 320, demodulators 322, and modulators 324. The RF transponder 318 may operate using RFID technology known in the art. Each RF transponder rectifier circuit 320 should be associated with a specific series and/or parallel resonant frequency to maximize signal voltage generated to power necessary sections of the tag during different modes of operation. The RF transponder 318 may be designed with one or more series and/or parallel resonant frequencies for the transponder demodulator 322 to properly control and sync the transponder control logic 326 and targeted locations of the memory 314. The RF Transponder 318 should be designed with one or more series and/or parallel resonant frequencies for the transponder modulator 324 to properly generate transmission signals externally to a reader (not shown) through the antenna 328. The RF transponder 318 should include all or a subset of the frequency bands supporting RFID as known in the art. The RF Transponder should be designed with safeguard features to ensure inappropriate operations do not occur based on safety requirements.

Referring back to FIG. 3A, the measurement logic 312 may support the input measurands 318 from the sensor 310 (sense loop), convert the measurand 318 values into a digital format, and write the values into targeted portions of the memory 314 on a data channel 334. The measurement logic 312 may support serial or parallel control 330 and clock 332 signals. The memory 314 may support, at minimum, non-volatile reference information (e.g., identification, encryption key) and non-volatile or volatile value fields (e.g., measurements). Further, the memory 314 may also support serial or parallel reads and writes. All demodulators 306, 322 may provide serial and/or parallel control and clock signals. The logic controller 326 may provide read capabilities of the targeted memory 314 region and simultaneously input into the modulator 324.

It is important to note that the wireless communication tag may be designed to operate with any of the membrane corrosion sensors previously described—membrane or gasket membrane sensors that may optionally include fracture sensing. Additionally, the wireless communication tag may be designed to operate with any other sensor that may be installed to monitor a structure.

In one example, multiple structural sensors (e.g., gasket corrosion sensors) each have a wireless communication tag are installed in an aircraft structure and employed under an overall testing plan. The sensors are first installed at their various location during the aircraft build. A first reading is performed for all the sensors to validate their functioning and to provide identification and sensor results with a reader device. Following this, the aircraft build is completed and the sensors are then revalidated for functionality. (This sensor installation may occur during the original aircraft build or a retrofit during aircraft maintenance.) The identification and location of the various sensors are recorded. The sensors are next read at a scheduled inspection and any indicated problems repaired. An example reading process is described hereafter.

A wireless reader device is employed to read identification numbers of sensors by transmitting a "ping" to a localized area of the aircraft structure where one or more sensors are installed. Any sensors in the area respond with their identification numbers. The indentification numbers are then cross-referenced to aircraft records to determine the sensor locations. The reader then interrogates all the sensors by transmitting another "ping" to energize sense element circuitry of the sensors. Each sensor tag is powered by the voltage induced in it by the readers transmitted power. The wireless communication tag then verifies that the induced power is within system specifications. An error message is returned to the reader if this fails. If successful, the sense portion of the tag then energizes the conductor sense loop. The sense portion of the tag then reads electrical characteristics of the energized sense loop. The tag then transmits sense element readings to the reader for analysis. The reader then receives the transmitted tag data and compares the values to reference standards for the respective sensors. Finally, the reader displays the inspection results for each sensor. The next regular inspection is scheduled if the result is successful or a repair is scheduled if a failure is indicated.

5. Method of Sensing Potential Corrosion

Figure 4:
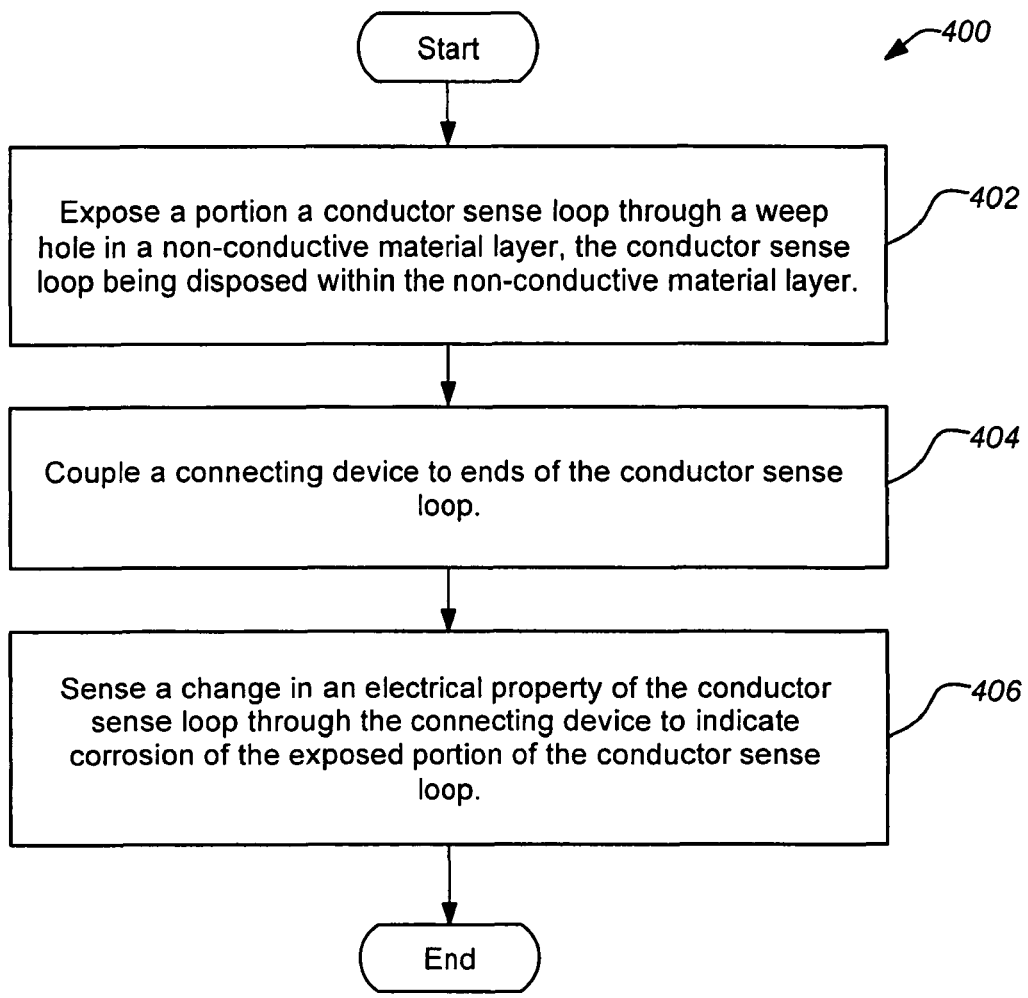
FIG. 4 is a flowchart of a method of sensing corrosion.

FIG. 4 is a flowchart of a method 400 of sensing potential corrosion. The method 400 begins with an operation 402 of exposing a portion a conductor sense loop through a weep hole in a non-conductive material layer. The conductor sense loop is disposed within the non-conductive material layer. Next in operation 404 a connecting device is coupled to ends of the conductor sense loop. Finally in operation 406, a change in an electrical property of the conductor sense loop is sensed through the connecting device to indicate corrosion of the exposed portion of the conductor sense loop. This method 400 for sensing corrosion may be modified consistent with any of the devices or other methods described herein. For example, the method 400 may be further enhanced by also including a fracture detection method as described below.

Figure 5:
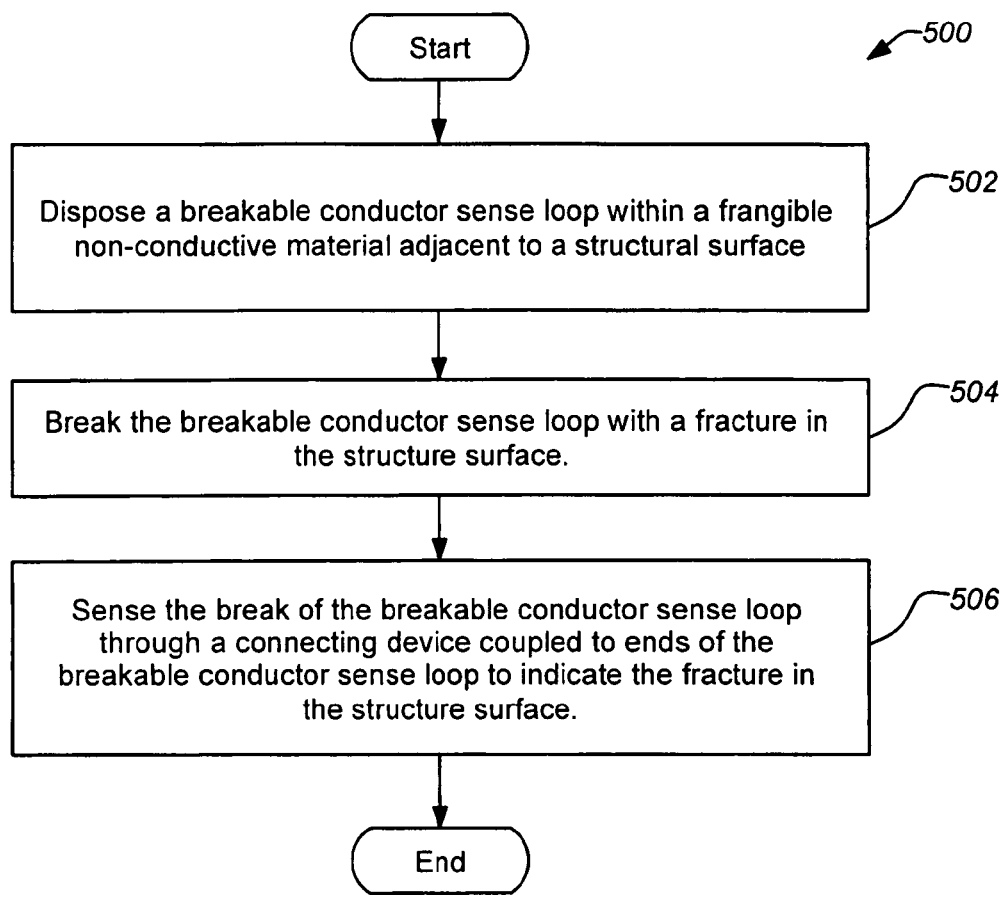
FIG. 5 illustrates an optional method for sensing fractures to be used with corrosion sensing.

FIG. 5 illustrates an optional method 500 for sensing fractures to be used with corrosion sensing. In this case, the non-conductive material layer is frangible and the conductor sense loop is breakable. The method 500 begins with a first operation 502 of disposing the breakable conductor sense loop within the frangible non-conductive material adjacent to a structural surface. Next, in operation 504 the breakable conductor sense loop breaks with a fracture in the structure surface. Finally, in operation 506 the break of the breakable conductor sense loop is sensed through a connecting device coupled to ends of the breakable conductor sense loop to indicate the fracture in the structure surface. This method 500 for sensing structural fractures may also be modified consistent with any of the devices or other methods described herein.

This concludes the description of various embodiments of the present invention. The foregoing description including the described embodiment of the disclosure has been presented for the purposes of illustration and description. It is not intended to be exhaustive or to limit embodiments of the invention to the precise forms disclosed. Many modifications and variations are possible within the scope of the foregoing teachings. Additional variations of the present disclosure may be devised without departing from the inventive concept as set forth in the following claims.

What is claimed is:

1. An apparatus for sensing corrosion, comprising:
   a non-conductive material layer disposed between a structural surface and a second structural surface in a gasket configuration such that both surfaces of the non-conductive material layer are sealed from moisture;
   a conductor sense loop comprising a fine wire within the non-conductive material layer and having a portion exposed through a weep hole in the non-conductive material layer, the conductor sense loop having ends; and
   a connecting device coupled to the ends of the conductor sense loop;
   wherein the exposed portion of the fine wire corrodes to induce a change in an electrical property of the conductor sense loop sensed through the connecting device.

2. The apparatus of claim 1, wherein the conductor sense loop corroding indicates potential corrosion of a near structural surface.

3. The apparatus of claim 1, wherein the non-conductive material layer comprises one or more sealing ribs against at least one of the structural surface and the second structural surface.

4. The apparatus of claim 1, wherein the non-conductive material layer comprises two layers sandwiching the conductor sense loop.

5. The apparatus of claim 1, wherein the non-conductive material layer comprises a resilient material.

6. The apparatus of claim 1, wherein the non-conductive material layer is bonded to a structural surface.

7. The apparatus of claim 1, wherein the connecting device comprises a wireless communications tag.

8. The apparatus of claim 1, wherein the conductor sense loop is routed around a fastener hole.

9. The apparatus of claim 1, wherein the non-conductive material layer comprises a frangible material.

10. A method for sensing corrosion, comprising the steps of:
    disposing a non-conductive material layer between a structural surface and a second structural surface in a gasket configuration such that both surfaces of the non-conductive material layer are sealed from moisture, the non-conductive material layer comprising a resilient material;
    exposing a portion a conductor sense loop comprising a fine wire through a weep hole in the non-conductive material layer, the conductor sense loop being disposed within the non-conductive material layer;
    coupling a connecting device to ends of the conductor sense loop; and
    sensing a change in an electrical property of the conductor sense loop through the connecting device to indicate corrosion of the exposed portion of the fine wire.

11. The method of claim 10, wherein the conductor sense loop corroding indicates potential corrosion of a near structural surface.

12. The method of claim 10, wherein the non-conductive material layer comprises one or more sealing ribs against at least one of the structural surface and the second structural surface.

13. The method of claim 10, wherein the non-conductive material layer comprises two layers sandwiching the conductor sense loop.

14. The method of claim 10, wherein the non-conductive material layer is bonded to a structural surface.

15. The method of claim 10, wherein the connecting device comprises a wireless communications tag.

16. The method of claim 10, wherein the conductor sense loop is routed around a fastener hole.

17. The method of claim 10, wherein the non-conductive material layer comprises a frangible material.

* * * * *